//

PHOTOGRAPHIC MATERIAL COMPRISING CYCLIC SULFONAMIDE SUBSTITUTED YELLOW COLOR COUPLERS

This invention relates to a colour photographic material having at least one silver halide emulsion layer, which material contains a novel yellow-forming coupler.

For producing colour photographic images, it is known to develop the exposed silver halide of a light-sensitive silver halide emulsion layer

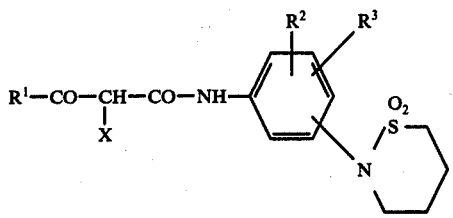

an aromatic developer containing a primary amino group in the presence of colour couplers. These colour couplers react with the oxidized colour developer to form a dye so that a dye image is obtained where there is developed silver.

In substrative three colour photography, it is customary to use a light-sensitive photographic multi-layered material which contains a red sensitized, a green sensitized, and a blue sensitive set of silver halide emulsion layers and in which layers colour development in the presence of suitable colour couplers gives rise to a cyan, a magenta and a yellow dye image, respectively.

The couplers used for producing the cyan dyes are usually phenols or naphthols, the couplers for forming the magenta dyes are usually pyrazolones and the couplers for forming the yellow dyes are usually open chain β-keto methylene compounds, and all couplers may contain in the coupling position a chemical group which is split off in the coupling reaction. The dyes formed by coupling are azomethines, indamines or indophenols, depending on the composition of coupler and of the developer.

The conventional yellow-forming couplers used are generally benzoyl acetanilides or alkoyl acetanilides such as pivaloyl acetanilides, in which one hydrogen atom of the active methylene group may be substituted by a group which is split off in the coupling reaction.

Conventional yellow couplers generally contain at least one group which confers diffusion resistance, generally a long chain alkoxy group or a sulphamyl or carbamyl group in which one or both hydrogen atoms may be substituted by alkyl groups, or an acylamino group which may be derived from a monoester of carbonic acid or from an aliphatic or aromatic carboxylic or sulphonic acid.

Many of the dyes produced from known couplers are unstable and undergo discoloration. The discoloration of the image dye due to the action of the light is known as bleaching while the discoloration due to exposure to elevated temperatures is referred to as yellowing. Yellow dyes produced from the known couplers are not completely satisfactory in their stability to light.

Thus, for example, dyes produced from the couplers described in German Offenlegungsschrift No. 2,263,587 undergo from 50 to 60% bleaching when exposed to 4.8 × $10^6$ lux hours.

It is therefore an object of the present invention to provide yellow-forming couplers which will be suitable for use in colour photographic materials and which, when subjected to chromogenic development, will give rise to yellow dyes substantially improved in their light-stability compared to known dyes.

The invention thus relates to a colour photographic material having at least one silver halide layer which material contains an acyl acetanilide yellow-forming coupler such as a benzoyl or alkoyl acetanilide yellow-forming coupler. The material according to the invention is characterized in that the yellow-forming coupler contains a cyclic 5-membered or 6-membered sulphonamide as substituent attached through its nitrogen atom to the phenyl ring of the aniline portion of the coupler.

When the yellow-forming couplers according to the invention are used in colour photographic materials, the dyes produced from them by exposure and chromogenic development are substantially improved in their stability to light due to the presence of the new cyclic sulphonamide group in the anilide portion of the yellow-forming coupler. This cyclic sulphonamide group may also be described as an alkanesultam group.

The method of preparation required for introducing the cyclic sulphamide group into yellow-forming couplers of the acyl acetanilide yellow coupler series for the purpose of increasing the light-stability of the dyes produced from the colour couplers is simple and trouble free. It may advantageously be carried out by first reacting an aromatic diamine with chloroalkylsulphochloride to convert it into the corresponding aniline containing the cyclic sulphonamide group, this substituted aniline being then used by known methods to prepare the desired acetanilide. The yellow-forming couplers used according to the invention may be unsubstituted on the active methylene group of the alkoyl or benzoyl acetanilides, or one hydrogen atom of the active methylene group may be substituted by a group which can be split off in the coupling reaction.

Examples of suitable cyclic 5-membered or 6-membered sulphonamide groups in the anilide portion of yellow-forming coupler compounds according to the invention include cyclotetramethylene sulphonamide, cyclotrimethylene sulphonamide and α-methyl cyclotetramethylene sulphonamide groups.

Particularly advantageous results are obtained when yellow-forming couplers of the following formula are used according to the invention:

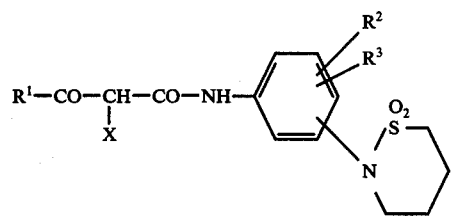

in which $R^1$ represents an aliphatic or aromatic group of the kind commonly found in the chemistry of yellow couplers, e.g. a phenyl group which may be substituted with an alkoxy group having up to 18 carbon atoms or a branched alkyl group such as t-butyl, phenylisopropyl or phenoxyisopropyl;

X represents hydrogen or a moiety which can be split off, of the kind commonly found in the chemistry of yellow-forming couplers and $R^2$ and $R^3$ which may be the same or different each represents hydrogen; an alkoxy group preferably having up to 18 carbon atoms, in particular up to 6 carbon atoms, such as a methoxy, propoxy, or isoamyloxy group; an aroxy group such as a naphthoxy or, preferably, phenoxy group; an alkyl group with up to 18 carbon atoms, in particular up to 6 carbon atoms, such as a methyl, isopropyl or cyclohexyl group; or halogen such as chlorine, bromine or fluorine, preferably chlorine.

The removable moiety may be any of the usual groups which can be split off in the process of chromogenic development by reaction with oxidized colour developer substances. These include groups which bring about a colour change in the coupler molecule when split off (as in the case of so-called masking couplers), groups which are capable of inhibiting further development when split off (as in the case of so-called development inhibitor releasing couplers) or groups which allow the colour image to develop using only 2-equivalents of silver per mol or coupler (as in the case of so-called 2-equivalent couplers) without at the same time bringing about a colour modifying or development inhibiting reaction as in the first two groups. When the groups have been split off, they may affect the diffusion resistance of the parent coupler (as in the case of couplers for the diffusion transfer process) or they may leave it unaffected.

The following are therefore examples of groups moieties which can be split off: Halogen such as fluorine, chlorine or bromine; the group OR, in which R represents an alkyl, aryl, heterocyclic or an acyl group; the group SB in which B represents an alkyl, aryl or heterocyclic group; an azo group or a heterocyclic 5-membered or 6-membered group having at least one nitrogen atom through which it is linked to the active methylene of the yellow coupler, e.g. cyclic acid imides or 5-membered heterocyclic unsaturated or aromatic groups such as pyrrole, diazole, triazole, thiazolone-2, oxazolone-2, pyridones, pyridazones, pyrimidinone-2 or pyrimidinone-6, pyrazinone-2, 4-hydroxypyridinone-2, 3-hydroxypyridazinone-6, 1,2,4- or 1,2,3-triazinone, 1,3-diazolone-2, 1,3,5-triazoles or 1,2,4-triazoles, 1,3,4,5-tetrazoles or 1,2,3,4-tetrazoles, 4-oxa-1,3-diazoles or 1,2,4-oxadiazoles or their derivatives including benzene condensed derivatives.

Groups of this kind are known and have been described, for example, in the following literature: U.S. Pat. Nos. 2,449,966; 2,584,349; 2,453,661; 3,227,550; 2,436,130; 3,447,928; 2,436,130; 3,447,928; 3,664,841; 3,865,506; 3,408,195 and 3,730,722; British Patent Specifications Nos. 1,331,179 and 1,351,424; German Offenlegungsschriften Nos. 2,213,416; 2,318,807; 2,414,006; 2,329,587; 2,433,812 and; 2,363,675; 2,441,779 and 2,442,703.

Examples of suitable yellow-forming couplers which may be used according to the invention are shown below:

1) 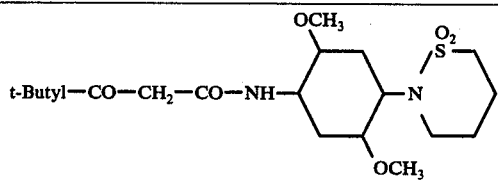

2) 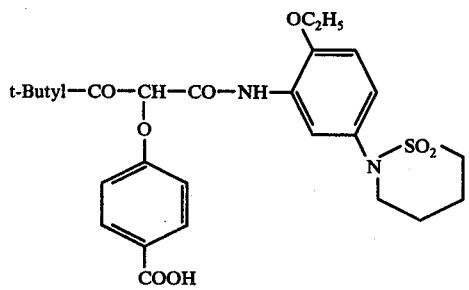

3) 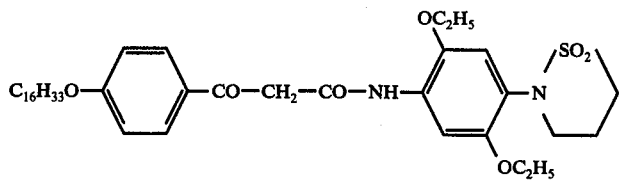

4) 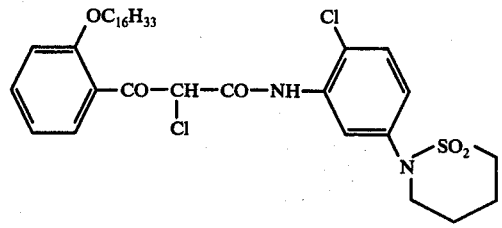

-continued

|   | A | | B | |
|---|---|---|---|---|
| | (phenyl ring with positions 2,3,4,5,6) —CO—CH(X)—CO—NH— (phenyl ring with positions 2',3',4',5',6') | | | |

| Coupler | A | X | B | |
|---|---|---|---|---|
| 5) | 4-OC$_{16}$H$_{33}$ | 3-(4-oxoquinazolinyl) | 2'-OCH$_3$, 5'-OCH$_3$; 4'-N(cyclic sulfonamide, SO$_2$ ring) | |
| 6) | 2-OC$_{16}$H$_{33}$ | imidazolyl-COOCH$_3$ | 2'-OCH$_3$, 5'-OCH$_3$; 4'-N(cyclic sulfonamide) | |
| 7) | 2-OC$_{16}$H$_{33}$ | 3-(4-oxoquinazolinyl) | 2'-OCH$_3$, 5'-OCH$_3$; 4'-N(cyclic sulfonamide) | |
| 8) | 4-OC$_{16}$H$_{33}$ | imidazolyl-COOCH$_3$ | 2'-OCH$_3$, 5'-OCH$_3$; 4'-N(cyclic sulfonamide) | |
| 9) | 2-OC$_{16}$H$_{33}$, 4-OCH$_3$ | CH$_3$OCO—(hydantoinyl, NH, =O) | 2'-OCH$_3$, 5'-OCH$_3$; 4'-N(cyclic sulfonamide) | |
| 10) | 2-OC$_{16}$H$_{33}$ | CH$_3$OCO—(hydantoinyl, NH, =O) | 2'-OCH$_3$, 5'-OCH$_3$; 4'-N(cyclic sulfonamide) | |

-continued
| | | | |
|---|---|---|---|
| 11) | 2-OC$_{16}$H$_{33}$ | 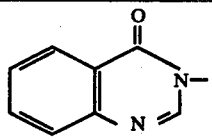 | 2'-OC$_2$H$_5$<br>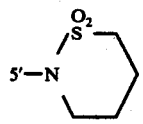 |
| 12) | 2-OC$_{16}$H$_{33}$ | 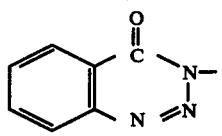 | 2'-OC$_2$H$_5$<br>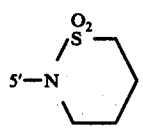 |
| 13) | 2-OC$_{16}$H$_{33}$ | 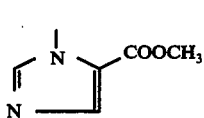 | 2'-OC$_2$H$_5$<br>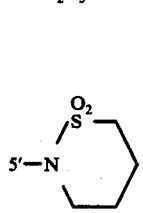 |
| 14) | 4-OC$_{16}$H$_{33}$ | 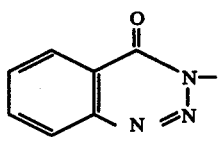 | 2'-OC$_2$H$_5$<br>5'-OC$_2$H$_5$<br>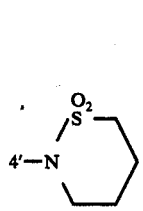 |
| 15) | 2-OC$_{16}$H$_{33}$ | H | 2'-OC$_2$H$_5$<br>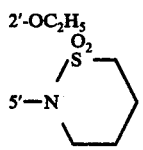 |
| 16) | 2-OC$_{16}$H$_{33}$ | Cl | 2'-OC$_2$H$_5$<br>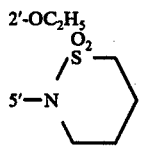 |
| 17) | 2-OC$_{16}$H$_{33}$<br>4-OCH$_3$ | H | 2'-OCH$_3$<br>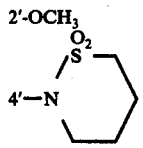<br>5'-OCH$_3$ |
| 18) | 2-OC$_{16}$H$_{33}$<br>4-OCH$_3$ | Br | 2'-OCH$_3$<br>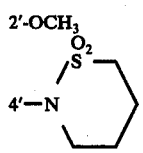<br>5'-OCH$_3$ |
| 19) | 2-OC$_{16}$H$_{33}$ | H | 2'-OCH$_3$ |

| | | | |
|---|---|---|---|
| | | | 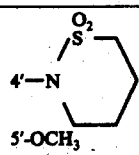
5'-OCH$_3$ |
| 20) | 2-OC$_{16}$H$_{33}$ | Cl | 2'-OCH$_3$ 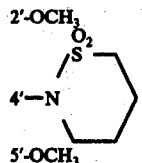
5'-OCH$_3$ |
| 21) | 4-OC$_{16}$H$_{33}$ | H | 2'-OCH$_3$ 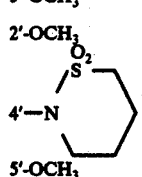
5'-OCH$_3$ |
| 22) | 4-OC$_{16}$H$_{33}$ | Cl | 2'-OCH$_3$ 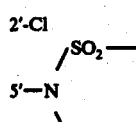
5'-OCH$_3$ |
| 23) | 4-OCH$_3$ | H | 2'-Cl 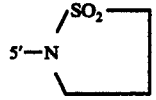 |
| 24) | 4-OCH$_3$ | Cl | 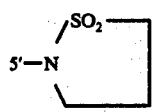 |
| 25) | 4-OCH$_3$ | 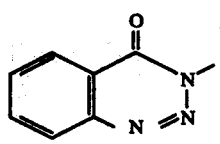 | 2'-C$_2$H$_5$ 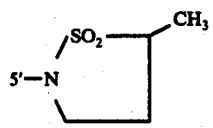 |
| 26) | 2,4-OCH$_3$ | H | 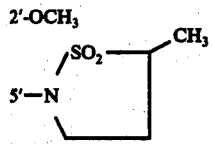 |
| 27) | 2,4-OCH$_3$ | Cl | 2'-OCH$_3$ 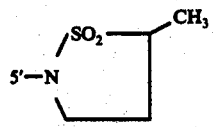 |
| 28) | 2,4-OCH$_3$ | 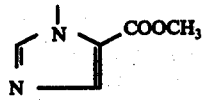 | 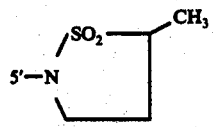 |

The new yellow-forming couplers can be prepared in known manner by reacting the corresponding anilines (see below) with benzoyl or alkoyl acetic acid esters. If it is desired to obtain 2-equivalent yellow-forming couplers, this reaction is followed in known manner by introduction of the required removable group. For example, the active methylene group may be halogenated and certain groups attached through oxygen or nitrogen may be introduced by reacting the halogenated couplers with phenols or heterocyclic compounds which contain an acidic NH group. Information about this may be obtained by reference to the literature mentioned above.

Preparation of the anilines is carried out, as already explained above, by reacting phenylene diamines with chloroalkylsulphochlorides by known methods, using a chloroalkyl sulphochloride in which the alkyl chain has 3 or 4 carbon atoms between the chlorine substituent and the sulphochloride group The alkyl chain may, of course, also be substituted by substituents which do not interfere with the ring closure reaction, for example short chained alkyl groups having up to 4 carbon atoms or benzyl. The couplers preferably contain, in the cyclic sulphonamide group, an unbranched alkyl chain having 3 or, in particular, 4 carbon atoms.

Preparation of Coupler 15

100 g of o-cetoxybenzoyl acetic ester of methyl alcohol and
65 g of 5-tetramethylene sulphonamido-2-ethoxyaniline are heated to boiling in
600 ml of anhydrous toluene, and a mixture of toluene and methanol is distilled off in a reaction time of about 5 hours. The reaction mixture is then stirred into propanol, cooled overnight and suction filtered, the residue obtained being recrystallised from n-propanol after purification with active charcoal. A second purification is carried out by recrystallisation from a ligroin/toluene mixture.
Yield: 105 g, m.p. 74° C.

Preparation of Coupler 16

60 g of coupler 15 was dissolved in
300 ml of methylene chloride. A mixture of
7.5 ml of sulphuryl chloride in
10 ml of methylene chloride is added dropwise to the boiling solution over a period of half an hour. The reaction solution is then concentrated by evaporation under vacuum. The yield is 65 g of oil. When recrystallised from a mixture of n-propanol and acetonitrile, it becomes a solid that has a melting point of 77°–78° C.

Preparation of Coupler 11

2.5 g of Coupler 16 are dissolved in
50 ml of acetonitrile.
7.8 g of quinazolinone and
4 g of sodium methylate are added. The reaction mixture is heated to boiling and after a reaction time of about 2 hours it is precipitated in a mixture of ice and hydrochloric acid. The residue is taken up in ethyl acetate, dried and concentrated by evaporation.

The thus concentrated residue is then taken up in ether and filtered over charcoal. A small quantity of petroleum ether is added and the mixture is cooled, filtered and the filtered-off product again recrystallised from ether. After suction filtration the product is washed with ether.
Yield: 11 g, m.p. 75° C.

Preparation of Coupler 12

20 g of coupler 16 are dissolved in
120 ml of acetonitrile.
5 g of 4-hydroxy-1,2,3-benzotriazine are added and the mixture is heated until a clear solution is obtained.

3.5 g of sodium methylate are then introduced and the mixture is stirred at 70° C for 2 hours.

The solution is then stirred into an ice hydrochloric acid mixture and the organic layer is taken up in ethyl acetate, if necessary with heating. The ethyl acetate layer is then evaporated to half its volume and cooled. The resulting precipitate is recrystallised from methanol.
Yield: 6 g, m.p. 122° C.

Preparation of Coupler 13

15 g of coupler 16 and 4 g of 3H-imidazole-4-carboxylic acid methylester are dissolved in
100 ml of acetonitrile.
3.5 g of sodium methylate are added.
10 ml of hexamethyl-phosphoric-acid-triamide and an additional
1 g of sodium methylate are added after a reaction time of 2 hours, and stirring is continued at, 60° to 70° C. The reaction solution is then introduced into an ice/hydrochloric acid mixture. The resulting precipitate is taken up in ethyl acetate, washed, dried and concentrated by evaporation. The residue is dissolved in ether, precipitated with petroleum ether, decanted and purified twice by the usual method of chromatography over silica.
Eluent: chloroform/acetone 3:2
Yield: 3 g, m.p.: 100°–101° C.

Preparation of Coupler 17

90 g of 2-cetyloxy-4-methoxybenzoyl acetic acid ester of methyl alcohol are heated to boiling in
200 ml of toluene.
57 g of 4-tetramethylene-sulphonamide-2,5-dimethoxyaniline are added. Anhydrous toluene is slowly added dropwise at the same time that a toluene/methanol mixture is distilled off. A further
15 g of the ester are added after a reaction time of 4 hours and the mixture is then heated to boiling for a further 2 hours. Toluene is then distilled off and the residue is stirred into methanol, cooled and suction filtered. Further purification is carried out by recrystallisation of the filtered-off product from ligroin and alcohol.
Yield: 85 g, m.p. 78° to 80° C.

Preparation of Coupler 18

60 g of Coupler 17 are heated to boiling in 300 ml of methylene chloride.
15.5 g of N-bromosuccinimide dissolved in
100 ml of anhydrous dioxane are slowly added dropwise.

After one hour, the reaction mixture is stirred into water and the insoluble residue is taken up in a suitable solvent and worked up in the usual manner.
Yield: 51 g of oil.

Preparation of Coupler 9

25 g of Coupler 18 are dissolved in
200 ml of hexamethyl phosphoric acid triamide and heated to 30° C together with
6 g of methoxycarbonyl-1,3-imidazolinone-2- and
13 ml of tetramethylguanidine. After a reaction time of 3 hours, the reaction mixture is precipitated in an ice/hydrochloric acid mixture and the residue is taken up in ether and worked up in the usual manner. The product is purified chromatographically over silica, using a 1:1 mixture of chloroform and ethyl acetate as eluant.

Yield: 2 g, m.p. 88°–90° C.

Preparation of Coupler 19

90 g of 0-cetoxybenzoyl acetic ester and
60 g of 4-tetramethylene-sulphonamido-2,5-dimethoxyaniline are heated to boiling in
500 ml of toluene and at the same time the toluene/alcohol mixture is distilled off. A further
10 g of o-cetoxybenzoylacetic ester are then added and toluene/alcohol continues to be distilled off under heating. The reaction solution is then stirred into alcohol and filtered. A small quantity of concentrated hydrochloric acid is added to the filtrate which is then cooled (2 days), suction filtered and washed with alcohol.

Yield: 81 g m.p. 56°–57° C.

Preparation of Coupler 20

50 g of Coupler 19 are heated to boiling in
300 ml of methylene chloride. A mixture of
63 ml of sulphuryl chloride in
20 ml of methylene chloride is added dropwise to the boiling solution over a period of half an hour. The solution is then stirred for another half an hour and concentrated by evaporation under vacuum.

Yield: 55 g of oil.

Preparation of Coupler 10

4 g of 4-methoxycarbonyl-1,3-imidazolinone-2 are dissolved in
50 ml of hexamethylphosphoric acid triamide and
8 ml of tetramethylguanidine, and a solution of
140 g of Coupler 20 in
40 ml of hexamethylphosphoric acid triamide is added at 30° C. After 2 hours, the reaction mixture is stirred into a mixture of ice and hydrochloric acid and worked up in the usual manner. The product is purified chromatographically over silica, using a 1:1 mixture of ethyl acetate and chloroform as eluant.

Yield: 0.5 g, m.p. 69°–70° C.

Preparation of Coupler 7

20 g of Coupler 20,
6.4 g of quinazolinone and
3.5 g of sodium methylate are heated to boiling in
180 ml of acetonitrile. The reaction mixture is stirred into ice/hydrochloric acid after about 2 hours and is then worked up in the usual manner and purified chromatographically over silica.

Eluent: ethyl acetate/chloroform 1:1,

Yield: 5.2 g, m.p. 79°–80° C.

Preparation of Coupler 6

20 g of Coupler 20,
55 g of imidazole carboxylic acid methyl ester,
120 ml of acetonitrile and
15 ml of tetramethylguanidine are heated to 40°–50° C and after a reaction time of about half an hour the mixture is heated to boiling. After a reaction time of about 8 hours, the reaction product is precipitated in a mixture of ice and hydrochloric acid and isolated in the usual manner. The product is purified by recrystallisation from methanol.

Preparation of Coupler 21

90 g of p-cetoxybenzoyl acetic ester of methyl alcohol and
60 g of 4-tetramethylene-sulphonamido-2,5-dimethoxyaniline are heated to boiling in
500 ml of toluene and at the same time a mixture of methanol and toluene is distilled off. When the reaction has been completed, the reaction mixture is poured into methanol and heated to boiling. The precipitate formed on cooling is washed with a small quantity of methanol and dried on clay. The crude product is recrystallised from acetone.

Yield: 75 g, m.p. 84°–85° C.

Preparation of Coupler 22

50 g of Coupler 21 are heated to boiling in
300 ml of methylene chloride and at the same time a solution of
6.3 ml of sulphuryl chloride in
30 ml of methylene chloride is added dropwise in the course of half an hour. The reaction solution is concentrated by evaporation and the product recrystallised from acetonitrile.

Yield: 48 g, m.p. 87°–88° C.

Preparation of Coupler 5

19 g of Coupler 22,
6.4 g of quinazolinone and
3.5 g of sodium methylate are heated to boiling in
180 ml of acetonitrile. When the reaction has been completed, the reaction mixture is precipitated in a mixture of ice-hydrochloric acid, suction filtered, washed with water and dried on clay. The residue is suspended in methanol, heated to boiling, cooled, suction filtered and recrystallised twice from alcohol.

Yield: 4.5 g, m.p. 84°–94° C.

Preparation of Coupler 8

21.5 g of Coupler 22,
5.5 g of imidazole carboxylic acid methyl ester in
120 ml of acetonitrile and
15 ml of tetramethylguanidine are heated to 40°–50° C. After a reaction time of about 6 hours, the reaction mixture is poured into water, acidified and taken up in ethyl acetate, worked up in the usual manner and purified chromatographically three times over silica. The eluants used were ethyl acetate/methanol 10:1 and ethyl acetate.

Yield: 1.5 g. m.p. 90°–94° C.

The new yellow-forming couplers are easily prepared and when used according to the invention they are surprisingly stable in storage. Compounds conforming to the above general formula have an excellent coupling activity that is to say they give rise to dye images which have a high colour density and high sensitivity and they are therefore eminently suitable for use in light-sensitive silver halide emulsion layers of single layered or multilayered colour photographic materials.

The yellow couplers need not necessarily be incorporated in light-sensitive layers but may be accommodated in a layer of binder adjacent to a light-sensitive silver halide emulsion layer.

The materials according to the invention may be, for example, positive, negative or reversal materials mounted on the usual support layers used for the preparation of photographic materials. Suitable materials for use as substrates include e.g. foils of cellulose nitrate, cellulose acetate such as cellulose triacetate, polystyrene, polyesters such as polyethylene terephthalate or polyolefines such as polyethylene or polypropylene, baryta coated paper substrates or polyolefine laminated paper substrates, e.g. polyethylene laminated paper, as well as glass or the like.

When preparing the light-sensitive colour photographic material, the diffusion resistant yellow-forming couplers can be incorporated by the known methods employed for emulsion techniques; for example water-soluble colour couplers, i.e. those which contain one or more water-solubilising groups such as sulpho groups or carboxyl groups (in the acid or salt form) may be incorporated as aqueous solutions while colour couplers which are not sufficiently water-soluble may be incorporated as solutions in suitable high boiling or low boiling organic solvents which may or may not be water-miscible or in mixtures of such solvents. Diffusion resistant hydrophobic yellow couplers may advantageously be introduced into gelatine solutions or directly into water with the aid of so-called oil formers, optionally with the addition of wetting agents. Diffusion resistant yellow couplers such as those described in U.S. Pat. Nos. 2,322,027 and 2,533,514, for example, may be incorporated in water-soluble photographic colloids by dissolving them in a water-insoluble organic solvent which has a relatively high boiling point, which may be mixed with a low-boiling auxiliary solvent, and then emulsifying or dispersing the solution in a photographic colloid solution.

The photographic colloid solution may be an aqueous, light-insensitive hydrophilic colloidal solution, in particular an aqueous gelatine solution, or it may be a completely prepared photographic emulsion mixture containing the necessary additives, in particular a light-sensitive silver halide emulsion. The diffusion resistant yellow couplers are preferably dissolved in a low boiling solvent which has a boiling point of not more than 130° C, optionally with the aid of an additional higher boiling solvent, and then emulsified in a hydrophilic phase in known manner, optionally in the presence of a wetting agent, using as hydrophilic phase an aqueous solution which may contain a colloid. The low boiling solvent is then practically removed completely so that the diffusion resistant yellow coupler is left uniformly distributed in the hydrophilic phase. The hydrophilic phase finally is added to the casting composition of the appropriate light-sensitive or light-insensitive photographic layer.

Further information about particularly suitable techniques for incorporating colour couplers in the hydrophilic colloid layers of a photographic material may be found in published Dutch Patent Application Nos. 6,516,423; 6,516,424; 6,600,098; 6,600,099 and 6,600,628; Belgian Patent No. 750,898; U.S. Pat. No. 2,304,940 and British Patent Specification No. 791,219.

Suitable low boiling solvents include e.g. esters such as ethyl acetate, formates such as ethyl formate, ketones such as methyl-n-propyl ketone, ethers such as diisopropylether, cyclohexane, toluene and diethylcarbonate.

The light-sensitive emulsions used may be the emulsions of silver halides such as silver chloride, silver bromide or mixtures thereof which may have a small silver iodide content of up to 10 mol %, in one of the usual hydrophilic binders.

The binder used for the photographic layer is preferably gelatine although this may be partly replaced by other film forming natural or synthetic polymers such as, for example, alginic acid and its derivatives such as its salts, esters or amides, carboxymethylcellulose, alkylcelluloses, starch and its derivatives, polyvinyl alcohol, copolymers containing vinyl alcohol and vinyl acetate units, polyvinyl pyrrolidone and the like, anionic polyurethanes and other latices, e.g. copolymers of acrylic esters, acrylonitrile and acrylamide, etc..

The light-sensitive emulsions may be chemically sensitized by carrying out the ripening process in the presence of small quantities of sulphur compounds such as allylisothiocyanate, allylthiourea, sodium thiosulphate, etc.. The light-sensitive emulsions may also be sensitized by the tin compounds described in Belgian Patent Nos. 493,464 and 568,687 or by means of polyamides such as diethylene triamine or the iminoaminomethanesulphinic acid compounds described in Belgian Patent No. 547,323 or by means of small quantities of noble metal compounds such as compounds of gold, platinum, palladium, iridium, ruthenium or rhodium. This method of chemical sensitization has been described in the article by R. Koslowsky, Z. Wiss. Phot. 46, 65–72 (1951). The emulsions may also be sensitized with polyalkylene oxide derivatives, e.g. with a polyethylene oxide having a molecular weight of between 1000 and 20,000 or with condensation products of alkylene oxides and aliphatic alcohols, glycols, cyclic dehydration products of hexitols, alkyl substituted phenols, aliphatic carboxylic acids, aliphatic amines, aliphatic diamines and amides. These condensation products have a molecular weight of at least 700 and preferably more than 1000. These sensitizers may, of course, be combined for the purpose of obtaining special effects, as described in Belgian Pat. No. 537,278 and British Patent Specification No. 727,982.

The emulsions containing the colour couplers may also contain spectral sensitizers, e.g. the usual monomethine or polymethine dyes such as cyanines, hemicyanines, streptocyanines, merocyanines, oxonoles, hemioxonoles, styryl dyes, etc. or trinuclear or higher nuclear methine dyes, for example rhodacyanines or neocyanines. Sensitizers of this kind have already been described, for example, in the work by F. M. Hamer "The Cyanine Dyes and Related Compounds" (1964), Interscience Publishers John Wiley and Sons, New York.

The emulsions may contain the usual stabilizers, e.g. homopolar or salt compounds of mercury containing aromatic or heterocyclic rings, such as mercaptotriazoles, simple mercury salts, sulphonium mercury double salts and other mercury compounds. Azaindenes are also suitable stabilizers, particularly tetra- or pentaazaindenes, especially those which are substituted with hydroxyl or amino groups. Compounds of this kind have been described in the article by Birr. Z. Wiss. Phot 47, 2–27 (1958). Other suitable stabilizers are e.g. heterocyclic mercapto compounds such as phenylmercapto tetrazole, quaternary benzothiazole derivatives, benzotriazole and the like.

The emulsions may be hardened in the usual manner, for example with formaldehyde for halogenated aldehydes containing a carboxyl group, such as mucobromic acid, diketones, methanesulphonic acid esters, dialdehydes and the like.

The photographic layers may also be hardened with epoxide hardeners, heterocyclic ethyleneimine hardeners or acryloyl hardeners. Examples of such hardeners have been described e.g. in German Offenlegungsschrift No. 2,263,602 or in British Patent Specification No. 1,266,655. The layers may also be hardened by the process according to German Offenlegungsschrift No. 2,218,009 to obtain colour photographic materials suitable for high temperature processing.

The photographic layers or colour photographic multilayered materials may also be hardened with hardeners of the diazine, triazine or 1,2-dihydroquinoline series as described in British Patent Specifications No. 1,193,290; 1,251,091; 1,306,544 and 1,266,655; French Patent Specification No. 7,102,716 or German Offenlegungsschrift No. 2,332,317. Examples of such hardeners include diazine derivatives containing alkyl or aryl sulphonyl groups, derivatives of hydrogenated diazines or triazines such as 1,3,5-hexahydrotriazine, fluorosubstituted diazine derivatives such as fluoropyrmidines and esters of 2-substituted 1,2-dihydroquinoline- or 1,2-dihydroisoquinoline-N-carboxylic acids. Vinyl sulphonic acid hardeners and carbodiimide and carbamoyl hardeners such as those described e.g. in German Offenlegungsschriften Nos. 2,263,602; 2,225,230 and 1,808,685; French Patent No. 1,491,807; German Patent No. 872,153 and DDR Patent Specification No. 7,218 are also suitable. Other suitable hardeners have been described, for example, in British Patent Specification No. 1,268,550.

The usual colour developers are used for producing the dyes, for example the usual aromatic compounds based on p-phenylenediamine and containing at least one primary amino group.

Suitable colour developers include, for example, N,N-dimethyl-p-phenylenediamine; N,N-diethyl-p-phenylenediamine; N-monoemethyl-p-phenylenediamine; 2-amino-5-diethylaminotoluene; N-butyl-N-ω-sulphobutyl-p-phenylenediamine; 2-amino-5-(N-ethyl-N-β-methanesulphonamidoethylamino)-toluene and the like. Other suitable colour developers have been described, for example, in J.Amer.Chem.Soc. 73, 3100–3125 (1951).

The invention is described in more detail in the Examples given below.

EXAMPLE 1

Couplers 1,2,5,6,7,9,10,11,13 and 14 were each processed by the method described below.

2 mMol of coupler were dissolved in 3 ml of ethyl acetate and, after the addition of 0.5 g of dibutylphthalate, the solution was emulsified in known manner in 20 ml of a 5% gelatine solution at 60° C with the help of 0.16 g of the sodium salt of dodecylbenzene sulphonic acid. The emulsion was then mixed with 85 g of a 75% gelatine solution containing 1.93 g of silver bromide in the form of a dispersion, and the mixture was diluted with water to a suitable viscosity for casting.

After the mixed emulsion had been cast on a transparent support layer of cellulose triacetate covered with an adhesive layer, the resulting material was exposed behind a grey step wedge and cut up into two samples. Both samples were developed for 18 minutes at room temperature in a colour developer containing 4-amino-3-methyl-N-ethyl-N-methane sulphonamideethylaniline as developer.

The resulting samples were then further processed in the usual manner by bleaching and fixing of the resulting yellow negative image. Yellow step wedges which had excellent absorption characteristics were obtained.

One colour wedge was then subjected to a light stability test in which the sample was exposed to 2.4 × 10$^6$ Lux hours in a xenon test apparatus.

The percentage reduction of colour density of the irradiated sample was then determined by comparing it to an unirradiated sample, the samples being measured at density values of 0.5 and 1.5 in each case.

The results are summarized in the following Table:

| Coupler | Loss of Dye in % | |
|---|---|---|
| | at D 0.5 | at D 1.5 |
| 1 | 23 | 19 |
| 2 | 25 | 21 |
| 5 | 24 | 20 |
| 6 | 18 | 12 |
| 7 | 22 | 24 |
| 9 | 26 | 13 |
| 10 | 33 | 16 |
| 11 | 28 | 22 |
| 13 | 20 | 19 |
| 14 | 29 | 15 |

For comparison, colour wedges containing the following comparison couplers instead of the couplers according to the invention were prepared in analogous manner:

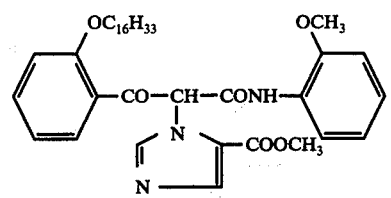

A

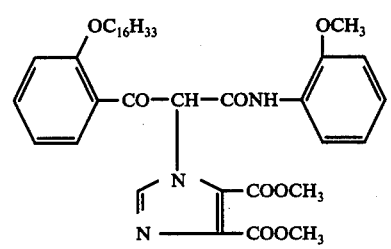

B

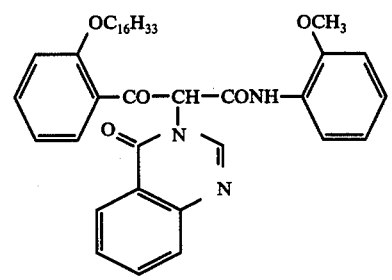

C

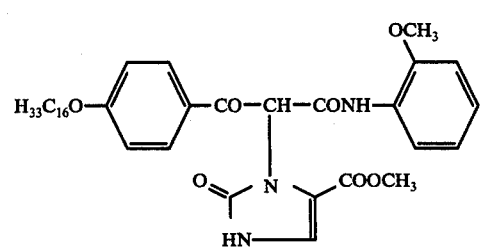

D

-continued

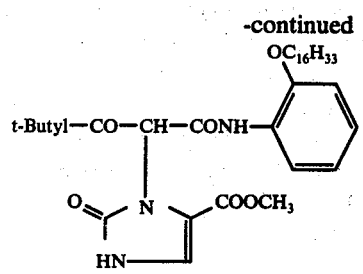
E

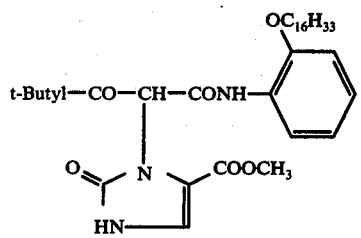
F

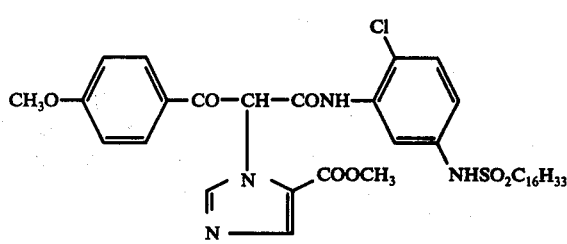
G

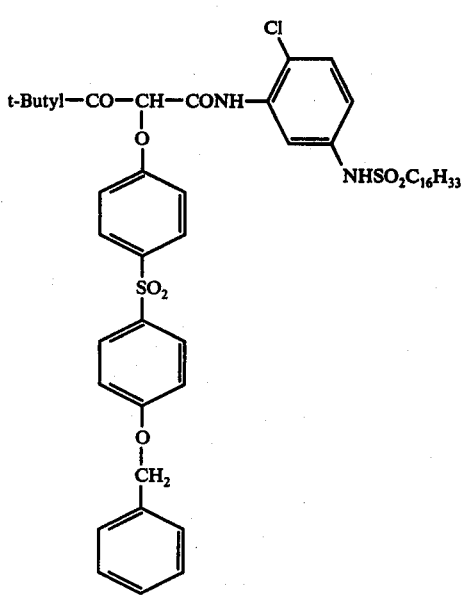
H

-continued

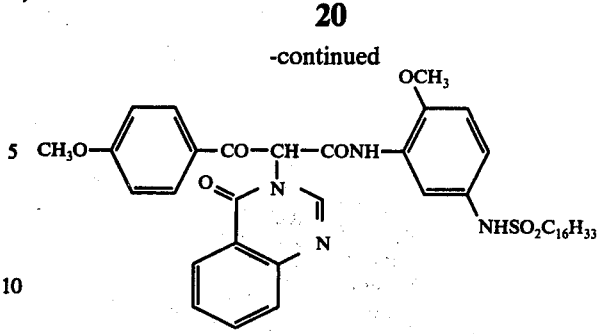
I

The results are summarized in the following Table:

| Comparison Coupler | Loss of dye in % | |
|---|---|---|
| | at D 0.5 | D 1.5 |
| A | 45 | 35 |
| B | 52 | 26 |
| C | 52 | 29 |
| D | 58 | 48 |
| E | 68 | 60 |
| F | 48 | 38 |
| G | 44 | 24 |
| H | 46 | 18 |
| I | 43 | 30 |

We claim:
1. Colour photographic material comprising at least one light-sensitive silver halide emuslion layer and containing in said silver halide emulsion layer or a layer adjacent thereto, a benzoyl or alkoyl acetanilide yellow-forming coupler, characterised in that the anilide ring has directly substituted on it the nitrogen of a cyclic alkylene sulphonamide group in which the cycle has 5 or 6 members.

2. Material as claimed in claim 1, in which the yellow-forming coupler is a compound corresponding to the following formula
in which
   $R^1$ represents an aliphatic or aromatic group;
   X represents hydrogen or a group which can be split off during colour development and
   $R^2$ and $R^3$ which may be the same or different and represent each a substituent selected from the group consisting of hydrogen, alkoxy, aroxy, alkyl or halogen.

3. Material as claimed in claim 2, in which $R^1$ represents a phenyl group or a t-butyl group.

4. Material as claimed in claim 2, in which $R^1$ represents phenyl substituted with an alkoxy group having up to 18 carbon atoms or t-butyl and $R^2$ and $R^3$ represent each a substituent selected from the group consisting of hydrogen, chlorine or alkoxy having up to 6 carbon atoms.

* * * * *

UNITED STATES PATENT OFFICE
CERTIFICATE OF CORRECTION

PATENT NO. : 4,095,983
DATED : June 20, 1978
INVENTOR(S) : Erich Wolff et al

It is certified that error appears in the above-identified patent and that said Letters Patent are hereby corrected as shown below:

Column 20, between lines numbered 37 and 38, the following formula should be inserted:

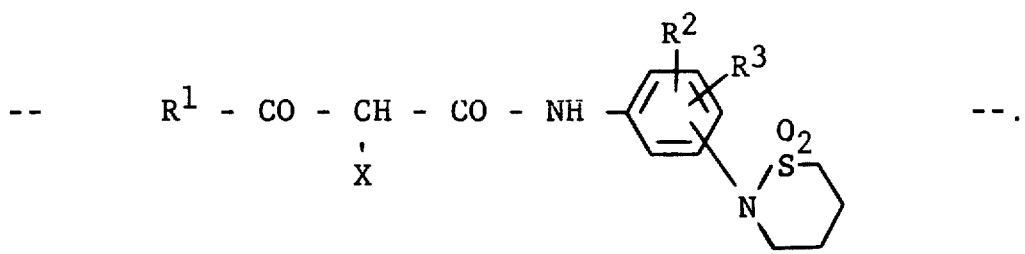

Signed and Sealed this

Sixth Day of March 1979

[SEAL]

Attest:

RUTH C. MASON
Attesting Officer

DONALD W. BANNER
Commissioner of Patents and Trademarks